(12) United States Patent
Yamanouchi et al.

(10) Patent No.: US 8,877,026 B2
(45) Date of Patent: Nov. 4, 2014

(54) ELECTRODE ASSEMBLY

(75) Inventors: Hisashi Yamanouchi, Osaka (JP);
Hiromi Ohkawa, Joyo (JP); Koji Ueda,
Kyotanabe (JP)

(73) Assignee: Horiba, Ltd. (JP)

( * ) Notice: Subject to any disclaimer, the term of this patent is extended or adjusted under 35 U.S.C. 154(b) by 75 days.

(21) Appl. No.: 13/435,897

(22) Filed: Mar. 30, 2012

(65) Prior Publication Data
US 2012/0247955 A1 Oct. 4, 2012

(30) Foreign Application Priority Data

Mar. 31, 2011 (JP) ................. 2011-081080

(51) Int. Cl.
*G01N 27/333* (2006.01)
*G01N 27/403* (2006.01)
*G01N 27/28* (2006.01)
*G01N 27/414* (2006.01)

(52) U.S. Cl.
CPC ............ *G01N 27/283* (2013.01); *G01N 27/414* (2013.01)
USPC .......................................... 204/416; 257/253

(58) Field of Classification Search
USPC .......................................... 204/416; 257/253
See application file for complete search history.

(56) References Cited

U.S. PATENT DOCUMENTS 5,833,824 A 11/1998 Benton
2005/0072672 A1 * 4/2005 Hoorn ........................... 204/416

FOREIGN PATENT DOCUMENTS

| DE | 4132432 A1 | 4/1993 |
| EP | 1396718 A1 | 3/2004 |
| JP | 7-36054 U | 7/1995 |
| JP | 09005287 A | 1/1997 |
| JP | 2001235446 A | 8/2001 |
| JP | 2002228628 A | 8/2002 |
| JP | 2003-344352 A | 12/2003 |
| JP | 2010-101864 A | 5/2010 |
| JP | 2010101864 A * | 5/2010 |
| WO | 98/21572 A1 | 5/1998 |
| WO | 2010/017192 A1 | 2/2010 |

OTHER PUBLICATIONS

Extended European Search Report for Application No. 12162782.2-2204, dated Jul. 23, 2012.
W. Oelbner et al., "Encapsulation of ISFET sensor chips", Sensors and Actuators B: Chemical, vol. 105, pp. 104-117, Feb. 14, 2005.
Japanese Office Action dated Jun. 24, 2014 issued in Japanese patent application No. 2011-081080, with English summary.

\* cited by examiner

*Primary Examiner* — Luan Van
*Assistant Examiner* — Steven Rosenwald
(74) *Attorney, Agent, or Firm* — Cantor Colburn LLP (57) ABSTRACT

The electrode assembly is provided with: a rod-like body 1 that extends along a predetermined axis; a substrate that is formed with a through-hole penetrating between a front surface and a back surface and attached to a fore end part of the body; and a sensor chip for electrochemical measurement, which is attached on the back surface of the substrate such that a sensing part is exposed outside from the through-hole, wherein: on the back surface of the substrate, a wiring for obtaining an output signal from the ISFET chip is formed, and the sensor chip is attached to the wiring directly or closely; and the substrate is attached with being inclined with respect to the predetermined axis of the body, and thereby the front surface of the substrate forms at least a part of a fore end surface that is inclined with respect to the predetermined axis.

4 Claims, 9 Drawing Sheets

ELECTRODE ASSEMBLY

TECHNICAL FIELD

The present invention relates to electrode bodies that respectively use sensor chips for electrochemical measurement and include: a measuring electrode and the like that are used to measure pH, various ionic species, electric conductivity, redox potential, and/or the like; a reference electrode that serves as a reference for electrode potential calculation or electrochemical measurement; and a combination electrode that is combined with the measuring electrode.

BACKGROUND ART pH sensors includes one that is miniaturized by using, not a conventional glass electrode but an ISFET (Ion Sensitive Field Effect Transistor) chip that is a sort of sensor chip for electrochemical measurement. For example, a pH sensor described in Patent literature 1 is configured such that a thorough-hole is formed through a wider width side surface of a body having a substantially flat rectangular parallelepiped shape, and from the through-hole, a sensing part of an ISFET chip is exposed. This pH sensor is one that is placed sideways on a desk or the like, and measures pH by dropping a minute amount of sample liquid into the through-hole with a dropper or the like, or is used with the through-hole and the ISFET chip being immersed in a liquid measuring object.

Figure 8:
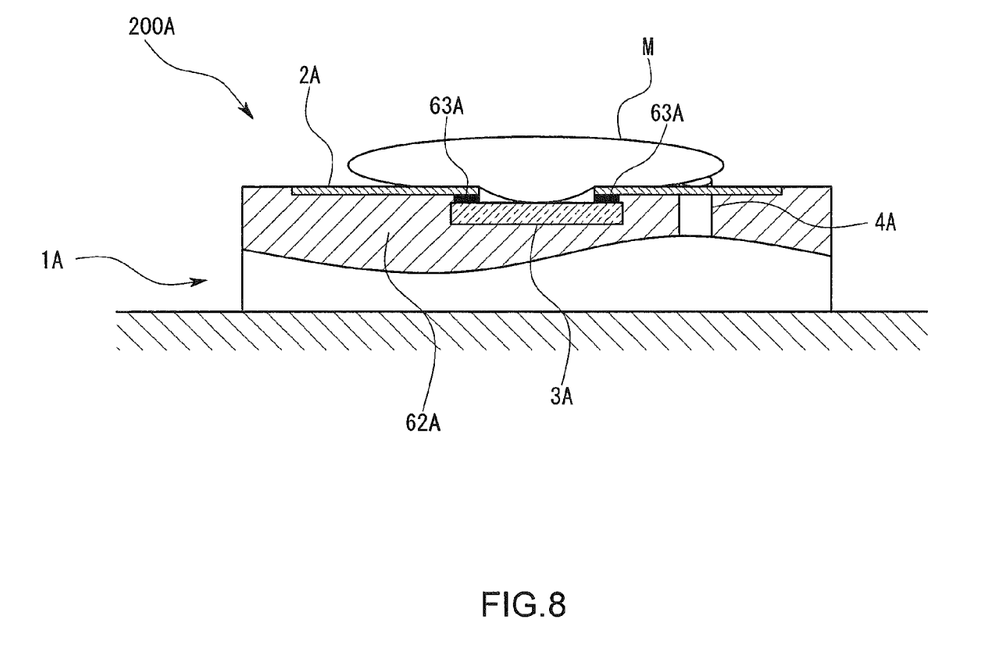
FIG. 8 is a schematic diagram illustrating an example of a conventional flat plate type pH sensor.

Also, pH sensors 200A that are configured to be placed on a desk or the like as the pH sensor 200A described above and bring a measuring object into contact with a sensing part of an ISFET chip 3A include a pH sensor 200A described in Patent literature 2. This pH sensor 200A is configured to make it easy to bring a solid such as skin into contact with a sensing part of an ISFET chip 3A, and in order to decrease a thickness thereof, configured such that, as illustrated in a partial cross-sectional view of FIG. 8, a front side of a thin substrate 2A is set as a surface that comes into contact with a measuring object M, and the ISFET chip 3A is attached on a back surface of the thin substrate 2A so as to expose the sensing part from a through-hole. Also, on the back surface of the thin substrate 2A, wiring for taking out an output signal from the ISFET chip 3A is surface-mounted. Such a configuration is also presented in the pH sensor 200A described in Patent literature 1. That is, it turns out that the configuration in which the ISFET chip 3A is attached on the back surface of the substrate 2A is used in the case where there is a technical subject of desirably decreasing the thickness of the pH sensor 200A or making it easy to come into contact with the measuring object M, in particular, in the case of configuring the pH sensor 200a of a flat plate type.

Meanwhile, the pH sensor 200A as described above is intended to be placed and move the measuring object M to the pH sensor 200A side to make the measurement; however, even in a probe type pH sensor 200A that is mainly intended to be moved, and immersed in or brought into contact with the measuring object M by a measurer, the ISFET chip 3A may be used.

Figure 9:
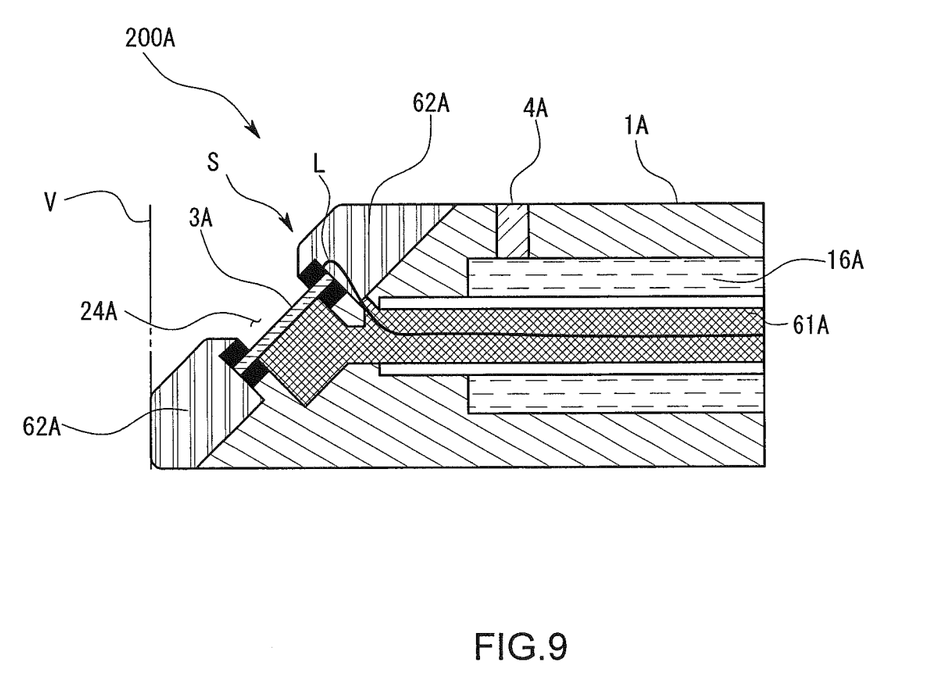
FIG. 9 is a schematic diagram illustrating another example of a conventional probe type pH sensor.

Further, Non-patent literature 1 describes a pH sensor 200A that is formed in a similar manner as that for the above-described one, and intended to prevent the measurement from being blocked by air bubbles that cover a sensitive part of an ISFET chip 3A when the pH sensor 200A is immersed in a liquid measuring object. As illustrated in FIG. 9, this pH sensor 200A is configured such that a fore end surface S formed in a fore end part of a rod-like body 1A is formed so as to form an angle of 45 degrees with a virtual plane V that is vertical to an axial direction of the body 1A, and in the central part of the fore end surface S, the ISFET chip 3A is arranged. More specifically, a lead L connected to the ISFET chip 3A is sealed in a space near a central axis of the body 1A by a first sealing material 61A, and in order to completely insulate the lead L that is drawn to an upper part of the ISFET chip 3A placed on the fore end surface S, a second sealing material 62A is placed around the ISFET chip 3A to thereby form the fore end surface S. In addition, internal liquid 16 is contained in a space around it, and a liquid junction part 4A that electrically connects the internal liquid 16A and a measuring object M to each other is formed in a side surface part of the body 1A. As described, the probe type pH sensor 200A is not required to be thinly configured like the above-described flat plate type pH sensor 200A, so that an output from the ISFET chip 3A is taken out by the lead L, and the lead L is insulated by placing the sealing material such as epoxy resin.

However, even in the above-described pH sensor 200A, it is difficult to prevent air bubbles from accumulating in the sensing part of the ISFET chip 3A on the fore end surface S at the time of liquid immersion. The present inventors have extensively examined the reason why such a phenomenon occurs, and as a result, first found that, in order to insulate the lead L connected to the ISFET chip 3A from the measuring object, the sealing material is placed, so that as illustrated in FIG. 9, a hole from the fore end surface S to a part where the sensing part of the ISFET chip 3A is exposed becomes deeper, and thereby sometimes, air bubbles supposed to move away along an incline of the fore end surface S accumulate in the hole to block the measurement from being made.

CITATION LIST

Patent Literature

Patent literature 1: JPU H07-36054
Patent literature 2: JPA 2010-101864

Non-Patent Literature

[Non-patent literature 1] W. Oelβner, et el., Sensors and Actuators B CHEM (2004), Encapsulation of ISFET sensor chips

SUMMARY OF INVENTION

Technical Problem

The present invention is made in consideration of the problem as described above and also made on the basis of the knowledge that was first found by the present inventors, and an object thereof is to provide an electrode assembly that can, even in a state where the electrode assembly is immersed in a liquid measuring object, prevent measurement more preferably than before from being blocked by accumulation of air bubbles on a surface of a sensor chip for electrochemical measurement.

Solution to Problem

That is, the electrode assembly of the present invention is provided with: a rod-like body that extends along a predetermined axis; a substrate that is formed with a through-hole penetrating between a front surface and a back surface and attached to a fore end part of the body; and a sensor chip being provided between the body and the substrate and attached on the back surface of the substrate such that a sensing part is exposed outside from the through-hole, wherein: on the back surface of the substrate, wiring for obtaining an output signal from the sensor chip is formed, and the sensor chip is attached to the wiring directly or closely; and the substrate is attached with being inclined with respect to the predetermined axis of the body, and thereby the front surface of the substrate forms at least a part of a fore end surface that is inclined with respect to the predetermined axis.

Here, the "electrode assembly" refers to a concept including: a measuring electrode and the like that are used to measure pH and/or various ionic species; a reference electrode that serves as a reference for electrode potential calculation or electrochemical measurement; and a combination electrode that is combined with the measuring electrode. Further, the reference electrode is one referred to as, for example, a comparison electrode or the like, and refers to a concept including them. Also, "the sensor chip is attached to the wiring directly or closely" refers to a concept including: a state where the sensor chip and the wiring are in direct contact with each other; and also a state where for example, between the wiring and the sensor chip, an extremely small gap is formed, and they are provided closely and electrically connected to each other through solder or the like. Further, the sensor chip for electrochemical measurement refers to a concept including various types of sensor chips for electrochemical measurement such as sensor chips for ion concentration measurement, electrolyte concentration (conductivity) measurement, and ORP (redox potential) measurement.

If so, the substrate is attached with being inclined with respect to the predetermined axis of the body, and thereby the front surface of the substrate is configured to form the fore end surface that is inclined with respect to the predetermined axis, so that even in the case of directing downward and immersing the front surface of the substrate in a liquid measuring object, generated air bubbles can be moved away along the incline of the fore end surface. Further, on the back surface of the substrate, the wiring for obtaining the output signal from the sensor chip is formed, and also the sensor chip is attached to the wiring directly or closely, so that a distance from the fore end surface to the sensor chip can be made substantially equal to a depth of the through-hole, i.e., a thickness of the substrate. That is, the through-hole can be formed as a very shallow hole, so that the fore end surface and the sensor chip can be arranged on substantially the same plane to, at the time of measurement, make it difficult for air bubbles to accumulate in the through-hole. To describe this from another perspective, in the present invention, based on the above-described configuration, providing a lead in order to take out the output signal from the sensor chip is not required, and accordingly, placing a sealing material in order to keep insulation of the lead as in the conventional case is not required, so that the depth of the through-hole for exposing the sensor chip can be made very shallow.

As described, the air bubbles can be moved away along the incline of the fore end surface, and also the through-hole for exposing the sensor chip can be formed to have a very shallow depth, so that even if the air bubbles having moved away along the fore end surface move in the through-hole, they can be made unlikely to be caught in the through-hole. Accordingly, the air bubbles hardly accumulate on the front surface of the sensor chip, and therefore the measurement can be prevented more preferably than before from being interrupted by the air bubbles.

As a preferable configuration to, even if air bubbles move in the through-hole, make the air bubbles move out of the through-hole, it is only necessary to provide a configuration in which an incline is formed from a rim to a central part on a back surface side of the through-hole by a filling material that makes a connection between the back surface of the substrate and the sensor chip. If so, as compared with the case where a simple through-hole is formed between the front and back surfaces of the substrate, a level difference can be decreased, and therefore the air bubbles having moved in the through-hole along the incline can be easily moved away.

As a specific configuration to decrease a thickness of the substrate so as to be able to shallow the depth of the through-hole as much as possible, and also make it each to attach the body and the substrate to each other without any gap, it is only necessary to provide a configuration in which the fore end part of the body has an outer circumferential portion that protrudes toward a fore end side of the body along the predetermined axis; a back surface outer edge portion of the substrate is attached to the outer circumferential portion; and relay wiring that is contained inside the body, extends from a base end side to the fore end side of the body, and is connected to the back surface of the substrate is further provided. If so, for example, the substrate and the relay wiring are not integrally formed as a flexible printed board, and the relay wiring provided as a separate body is connected to the back surface of the substrate to prevent the relay wiring from interfering with the outer circumferential portion of the body, so that the substrate can lid the fore end part of the body without any gap.

As specific embodiments to make it easier to move away air bubbles on the fore end surface include an embodiment in which an angle formed between a virtual plane that vertically intersects with the predetermined axis and the fore end surface is equal to 30 degrees or less.

To make it possible to easily obtain a reference potential from not only a liquid measuring object but, for example, a solid measuring object to make it easy to make a measurement, it is only necessary to provide a configuration in which inside the body, a containing part that contains an internal electrode and internal liquid is formed; and a liquid junction part that is formed with penetrating through the back surface and the front surface of the substrate from the containing part. For example, even in the case of a solid measuring object or a soft body such as agar or gelatin, air bubbles accumulate in a sensing part of a sensor chip in the conventional case; however, the present invention can solve such a problem as in the liquid case.

Advantageous Effects of Invention

As described, according to the electrode assembly of the present invention, the fore end surface formed by the front surface of the substrate is formed with being inclined with respect to the axial direction of the body, and also without use of a lead, the output signal from the sensor chip is adapted to be taken out by the wiring formed on the back surface of the substrate to be thereby able to shallow, as much as possible, the depth of the through-hole for exposing the sensor chip on the fore end surface, so that even in the case of immersion in a liquid measuring object, a situation where the measurement is blocked by accumulation of air bubbles in the exposed portion of the sensor chip can be prevented more surely than before.

REFERENCE SIGNS LIST

100: Probe (electrode assembly)
1: Body
16: Second containing part
19: Outer circumferential portion
2: Substrate
21: Front surface
22: Back surface
23: Wiring
24: First through-hole
3: ISFET chip
4: Liquid junction part
5: Relay wiring
62: Second filling material
621: Incline
C: Central axis (predetermined axis)
S: Fore end surface
V: Virtual plane

DESCRIPTION OF EMBODIMENTS

One embodiment of the present invention is described referring to the drawings.

Figure 1:
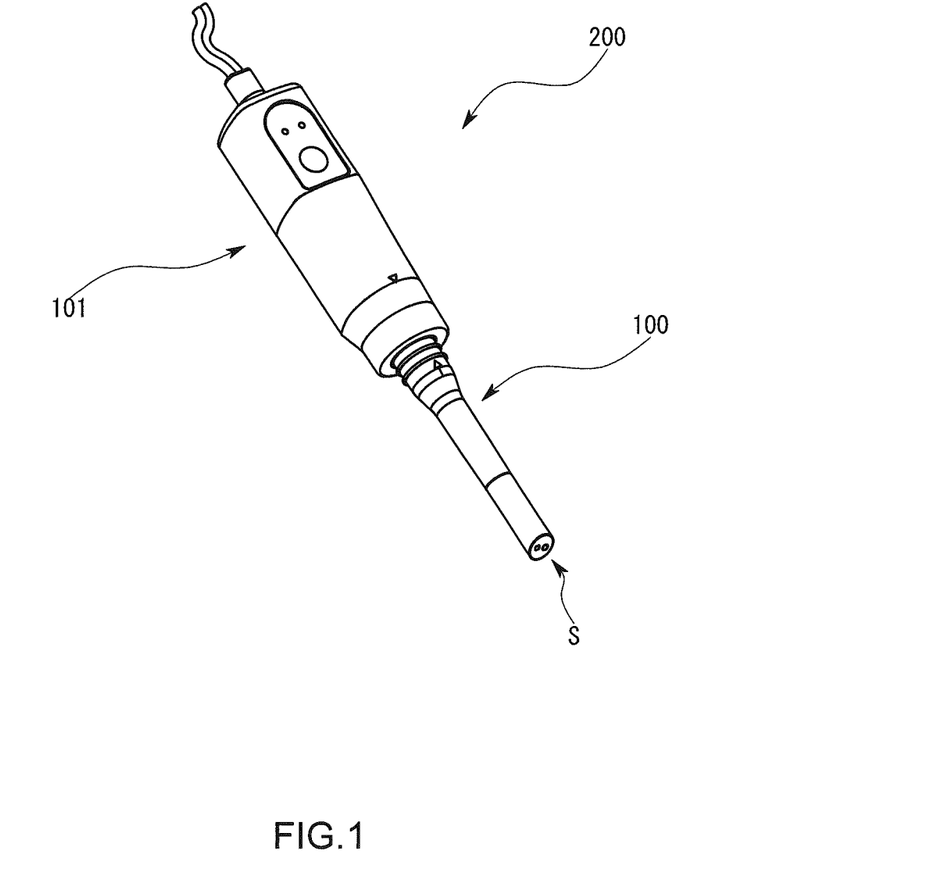
FIG. 1 is a schematic overall perspective view of a pH sensor according to one embodiment of the present invention.
Figure 2:
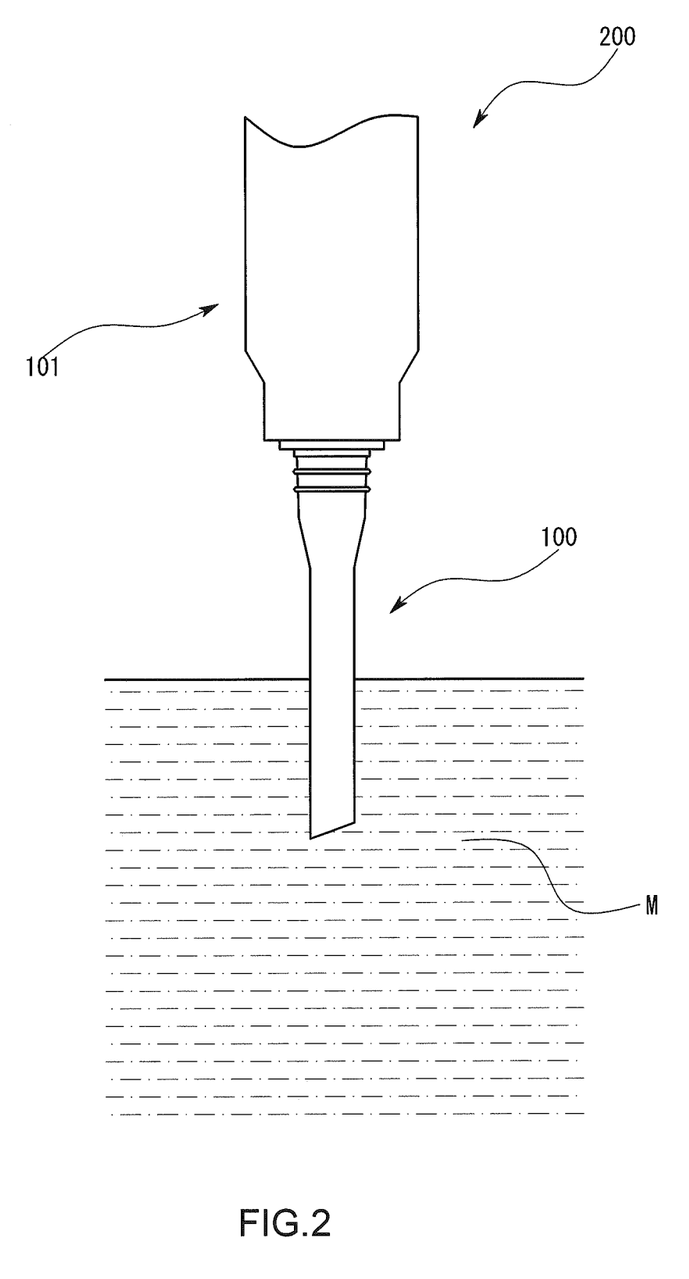
FIG. 2 is a schematic diagram illustrating a use state of the pH sensor in the same embodiment.

An electrode assembly of the present embodiment is a probe 100 that is, as illustrated in a perspective view of FIG. 1, formed as a combination electrode, and connected to a main body part 101 to thereby constitute a pH sensor 200. When used, the main body part 101 is grasped by a user, and as illustrated in FIG. 2, the pH sensor 200 is used with a fore end of the probe 100 being directed downward and a fore end surface S serving as a measuring part being immersed in, for example, a liquid measuring object M.

In the following description, the description is provided with a focus only on the probe 100.

Figure 3:
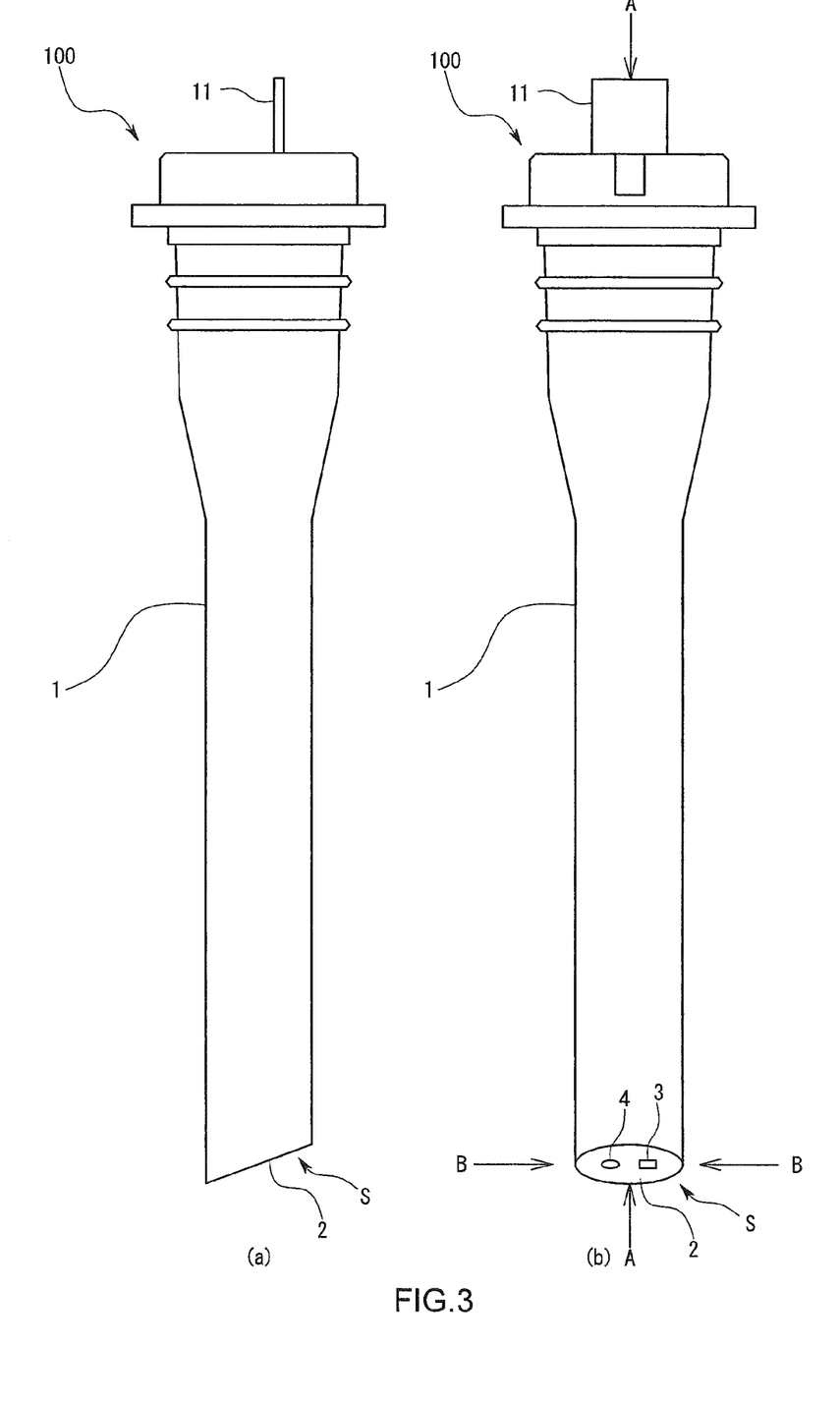
FIG. 3 is a schematic diagram that enlarges a probe part in the same embodiment.

The probe 100 is the combination electrode that combines a reference electrode serving as a reference for detecting an electrode potential and a measuring electrode for measuring a hydrogen ion concentration, and in order to configure the measuring electrode, uses an ISFET chip 3 that is a sort of sensor chip for electrochemical measurement. To briefly describe the ISFET chip 3 used to configure the measuring electrode, an ion sensitive film such as tantalum pentoxide is formed on a gate insulating film to form a sensing part. To describe an appearance of the probe 100, as illustrated in FIG. 3, a base end side is formed in a substantially thick cylindrical shape; a part from the central part to a fore end side is formed in a substantially thin cylindrical shape of which a diameter is thinner than that of the base end side; the fore end is partially cut off with respect to a direction in which the probe 100 extends; and thereby the fore end surface S is formed in an elliptical shape. More specifically, in a front view of FIG. 3 (a), the fore end of the probe 100 has a shape obtained by cutting a right triangle from a rectangle, and in a right side view of FIG. 3 (b), the fore end surface S is formed in the elliptical shape. On the fore end surface S, the measuring part is formed by exposing: a liquid junction part 4 serving as a part that is, in the reference electrode, brought into contact with the measuring object M; and the ISFET chip 3 constituting the measuring electrode.

Figure 4:
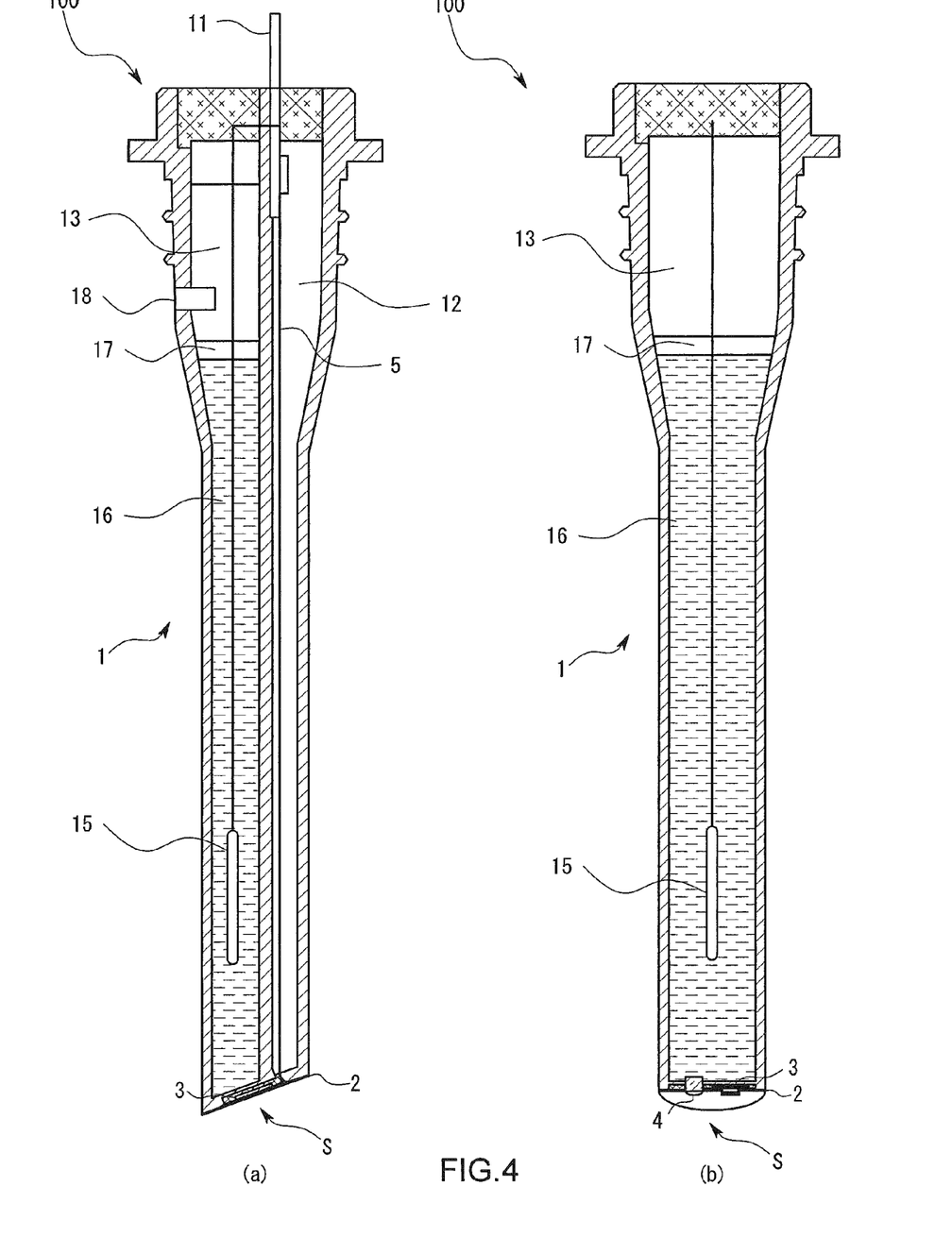
FIG. 4 is a schematic enlarged cross-sectional view of the probe part in the same embodiment.
Figure 5:
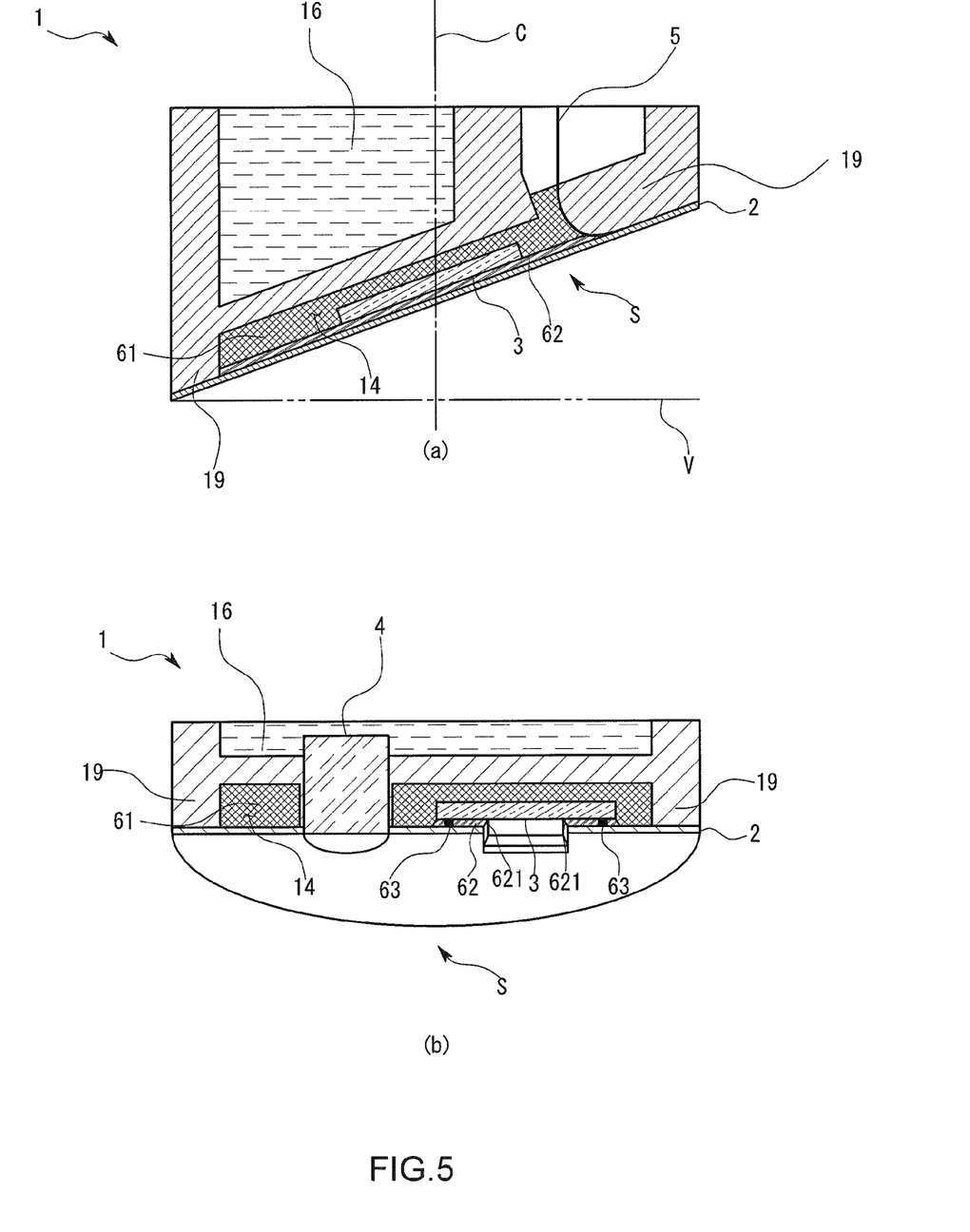
FIG. 5 is a schematic enlarged view of a probe fore end part in the same embodiment.

Next, a configuration of each component of the probe 100 is described. FIG. 4 illustrates cross-sectional views corresponding to the views of FIG. 3; FIG. 5 illustrates enlarged cross-sectional views of the fore end part of the probe 100; and FIG. 6 illustrates an exploded perspective view of the fore end part of the probe 100.

The probe 100 is provided with: a rod-like body 1 that extends along a predetermined axis; a substrate 2 of which a back surface 22 is attached to a fore end part of the body 1; and the ISFET chip 3 that is attached on the back surface 22 of the substrate 2 between the fore end part of the body 1 and the substrate 2. That is, the substrate 2 is bonded to the body 1 so as to lid the fore end of the body 1.

The body 1 is formed of nonpermeable resin, and as illustrated in the appearance views of FIG. 3, has a substantially two-stage cylindrical shape of which a fore end side extending along a central axis C corresponding to the predetermined axis is thinner than a base end side, and a fore end part thereof has a shape obtained by cutting the fore end part to form the substantially elliptical shape. Inside the body 1, as illustrated in the A-A cross-sectional view of FIG. 4 (a), two cavities are formed to form first and second containing parts 12 and 13, and in the fore end part of the body 1, as illustrated in FIG. 5, a concave portion 14 that contains the ISFET chip 3 and the like is also formed in the central part. Also, on the base end side of the body 1, a connecting terminal 11 that is connected to the main body part 101 is provided and adapted to transmit a signal from the ISFET chip 3 to the main body part 101.

Figure 6:
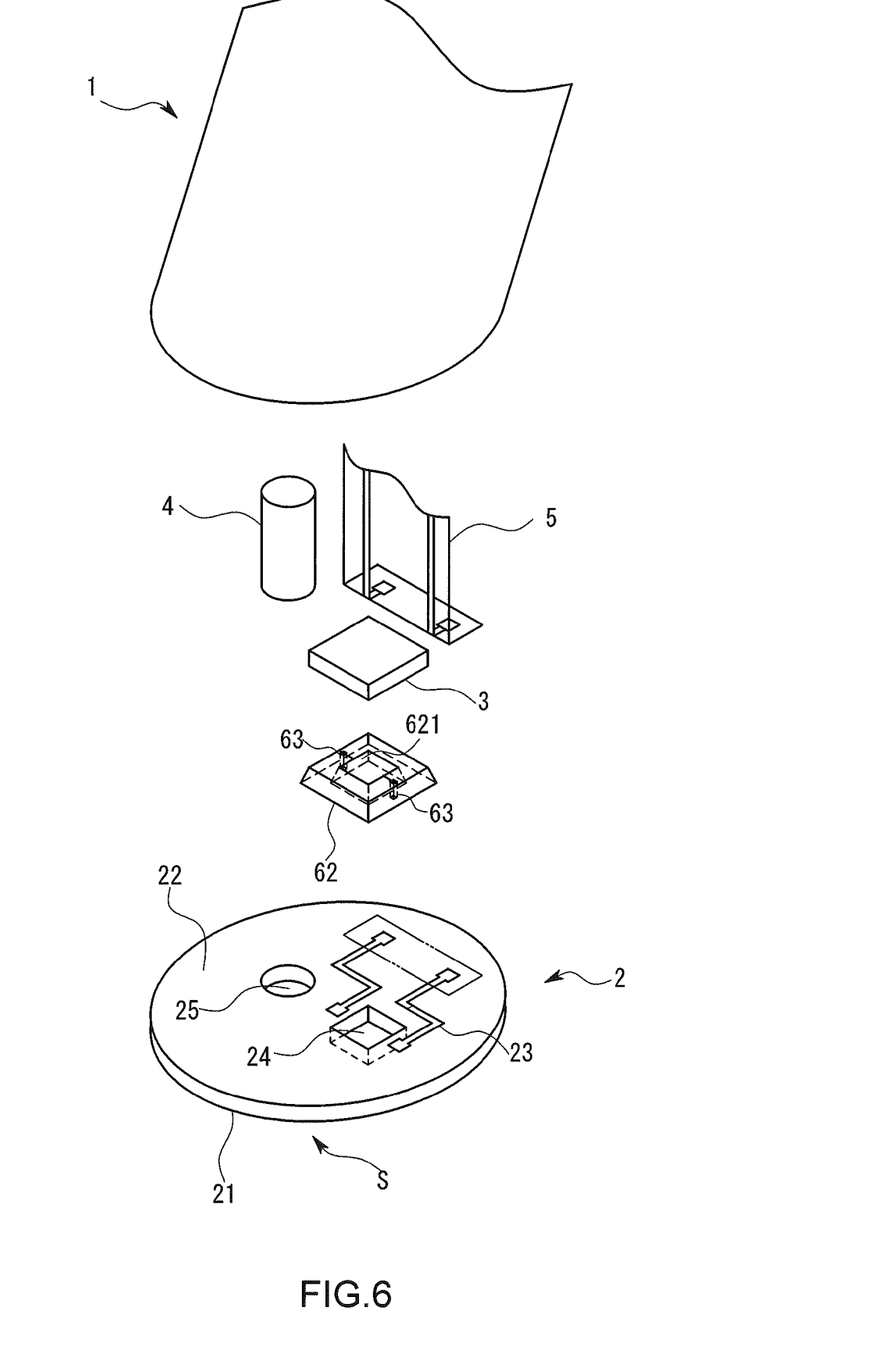
FIG. 6 is a schematic exploded perspective view of the probe fore end part in the same embodiment.

The first containing part 12 is a cavity that is illustrated on the right side of FIG. 4 (a) and FIG. 6 and extends in the axial direction, inside which, as illustrated in FIG. 6, a relay FPC 5 (Flexible Print Circuit) that relays the signal between the back surface 22 of the substrate 2 and the connecting terminal 11 is contained. Note that the relay FPC 5 corresponds to relay wiring in claims.

The second containing part 13 is a cavity that is illustrated on the left side of FIG. 4 (a) and extends in the axial direction; as can be seen from the A-A line cross-sectional view of FIG. 4 (a), has a volume that is made slightly larger than that of the first containing part 12; and is swelled out in a radial direction so as to slightly exceed the central axis C of the body 1. The second containing part 13 is one that contains: internal liquid 16 obtained by gelatinizing a KCl solution constituting the reference electrode; and a silver/silver chloride electrode 15 that is immersed in the internal liquid 16, and in a fore end part thereof, the liquid junction part 4 made of a porous material such as ceramics is formed. The liquid junction part 4 is, as illustrated in FIGS. 5(b) and 6, passed from the back surface 22 to a front surface 21 side of the substrate 2, and adapted to form substantially the same plane as the front surface 21 of the substrate 2. Also, a base end side of the internal liquid 16 is lidded by silicone gel 17, and a body 1 side surface on the base end side is formed with an inlet 18 for inletting the internal liquid 16 or the like into the second containing part 13 at the time of manufacturing. The inlet 18 is completely sealed by resin in a finished product.

The substrate 2 is one that is formed in a substantially thin-plate circular shape, and as illustrated in the enlarged views of FIGS. 5 (a) and (b), in the obliquely formed fore end part of the body 1, attached so as to lid the concave portion 14, and the front surface 21 thereof forms the fore end surface S of the probe 100. Also, as illustrated in FIGS. 1, 5 (b), and 6, in the substrate 2, a first through-hole 24 for exposing the sensing part of the ISFET chip 3 outside, and a second through-hole 25 for exposing one end of the liquid junction part 4 outside are formed with penetrating in a thickness direction in the central part. As illustrated in FIG. 5 (b), a back surface rim portion of the substrate 2 is bonded, in an airtight manner, to an outer circumferential portion 19 that is a part protruding in the central axis direction in the fore end part of the body 1, and a space between the concave portion 14 and the back surface 22 of the substrate 2 is sealed by a first sealing material 61 made of epoxy resin or the like to prevent liquid from intruding into the body 1 even in the case of immersing the body 1 in the liquid measuring object M. As a method for the bonding, for example, not only an adhesive but ultrasonic bonding may be used, and in this case, the body 1 and the substrate 2 can be preferably bonded to each other.

Also, between the substrate 2 and the body 1, the ISFET chip 3 is arranged, and in a space between a back surface 22 central part of the substrate 2 and a surface of the ISFET chip 3 where the sensing part is present, a second filling material 62 is filled for bonding. In the second filling material 62, the ISFET chip 3 is mounted on the substrate 2 by so-called flip-chip mounting so as to contain a conduction part of the ISFET chip 3 and solder bumps 63 for connecting wiring 23 formed on the back surface 22 of the substraten2 as illustrated in the perspective view of FIG. 6. Further, from a back surface side rim portion of the first through-hole 24 to the central axis side of the first through-hole 24, i.e., to the center of the sensing part of the ISFET chip 3, an incline 621 is formed by the second filling material 62 used for the flip-chip mounting. In other words, the first through-hole 24 is not formed as an abrupt vertical hole from the front surface 21 of the substrate 2 to the sensing part of the ISFET chip 3, but more continuously changes a depth from the front surface 21 of the substrate 2. For this reason, even if air bubbles intrude into the first through-hole 24 in the liquid, the air bubbles easily move away along the incline 621 to thereby more easily prevent the air bubble from accumulating around the sensing part.

Next, the fore end surface S that is formed by the front surface 21 of the substrate 2 with being inclined with respect to the extending central axis C of the body 1. As illustrated in FIG. 5 (a), the fore end surface S is configured to form a predetermined angle with the virtual plane V that vertical intersects with the central axis C of the body 1. In order to make it easy for air bubbles to move away in the case of directing downward and immersing the fore end surface S in the liquid measuring object M, it is only necessary to set the angle formed between the fore end surface S and the virtual plane V to 30 degrees or less. In the present embodiment, the angle is set to 20 degrees that is a preferable angle. As described, the fore end surface S is provided not as an end surface vertical to the axial direction of the body 1 but with being inclined, and therefore at the time of measurement, the air bubbles can be made to easily move away from the fore end surface S to outside along the fore end surface S.

Finally, features on a configuration as described above in which the substrate 2 flip-chip mounted with the ISFET chip 3 is attached to the fore end part of the body 1 are further described in detail.

Figure 7:
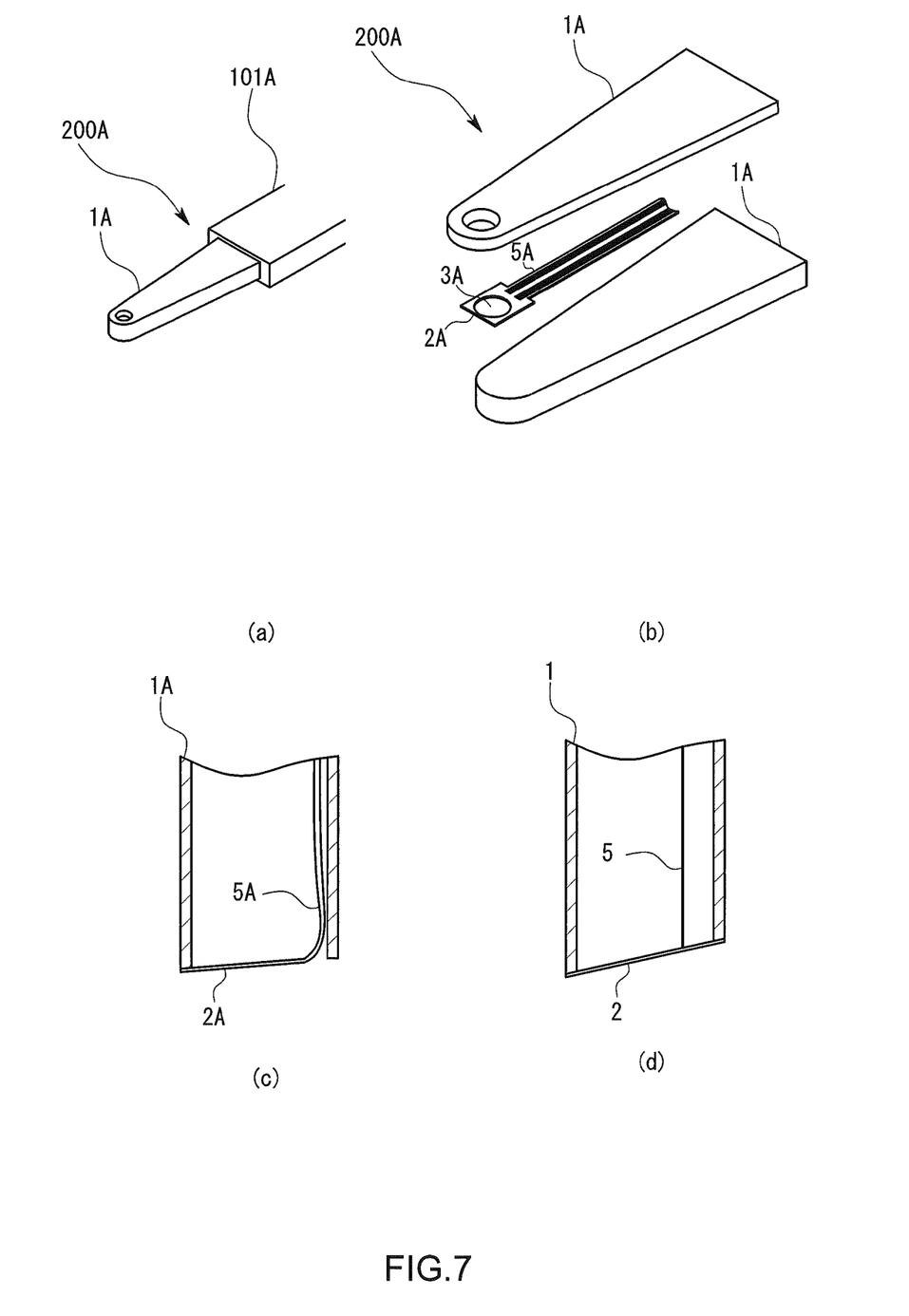
FIG. 7 is a schematic diagram illustrating features on connection between a body and a substrate in the same embodiment.

In the conventional flat plate type pH sensor 200A that is as illustrated in FIG. 7 (b) and described in Patent literature 1, in which the ISFET chip 3A is flip-chip mounted on the substrate 2A, in order to make it easy to form the pH sensor 200A in the flat plate shape as illustrated in the diagram, (shown in FIGS. 7(a) and 7 (b)) an object formed with a relay wiring 5A for transmitting the signal outputted from the ISFET chip 3A to the main body part 101A, and an FPC in which the relay wiring 5A is integrated on a side surface of the substrate 2A is used. In other words, in the conventional case, in the case of performing the flip-chip mounting, only the object in which the substrate 2A, the ISFET chip 3A, and the relay wiring 5A are mounted on one flexible board is used for the pH sensor 200A. For this reason, even in the case of attempting to lid the fore end part of the body 1A with use of the FPC flip-chip mounted with the ISFET chip 3A described in Patent literature 1, and thereby forming the fore end surface S as in the present embodiment, as illustrated in FIG. 7 (c), bending occurs in a relay wiring 5A part of the flexible board, and therefore a gap is formed in the radial direction. That is, the liquid of the measuring object M intrudes into the body 1A to cause various problems.

On the other hand, the present embodiment is adapted to form the substrate 2A to be flip-chip mounted with the ISFET chip 3, and the relay wiring 5 that transmits the output signal to the main body part 101 as separate bodies, and also connect one end of the relay wiring to not a side surface of the substrate 2 but the wiring 23 on the back surface with solder or the like, and therefore, as illustrated in FIG. 7 (d), the fore end part of the body 1 can be smoothly lidded by and attached to the substrate 2 without any gap. That is, by dividing the object, which was integrally formed in the conventional case, into the two members, the substrate 2A can be thinned as much as possible to shallow the first through-hole 24, and also attached to the body without any gap to form the fore end surface S.

According to the electrode assembly of the present embodiment configured as described, in the probe 100 type pH sensor 200, the fore end surface S is formed with being inclined with respect to the central axis C of the body 1; and the output signal from the ISFET can be transmitted to the relay FPC 5, the connecting terminal 11, and the main body part 101 not through a lead but through the wiring 23 that is surface-mounted on the back surface 22 of the substrate 2, and thereby the first through-hole 24 is formed to have a very shallow depth, so that as compared with the conventional pH sensor, air bubbles are highly unlikely to accumulate around the sensing part of the ISFET chip 3, and thereby problems such as interruption of measurement can be prevented from occurring.

Also, the fore end surface S is formed with being inclined with respect to the body 1 having the substantially cylindrical shape, and thereby formed in the elliptical shape, so that an area of the fore end surface S can be increased. Accordingly, a contact area with the measuring object M can be increased, or contrarily decreased by adjusting a size of the through-hole, and therefore a degree of freedom of design is high. In addition, the space between the fore end surface S and the fore end part of the body 1 can be widely ensured, and therefore the ISFET chip 3, the liquid junction part 4, other components, and the like are easily arranged.

Other embodiments are described.

In the above-described embodiment, described is the combination electrode in which the reference electrode and the measuring electrode are combined; however, the ISFET chip may constitute only the measuring electrode. Also, the reference electrode is not limited to that in the above-described embodiment, but may be a combination of internal liquid having the other constituents and an internal electrode. Further, a Pt film or the like may be formed on the fore end surface to form a pseudo-reference electrode for substituting the reference electrode.

Also, other examples of the ISFET chip include an example such as one in which Si, plastic, MgO, sapphire, or PET is used as a base material, on which an iridium oxide film is formed. Further, examples of the sensor chip for electrochemical measurement other than the ISFET chip include a sensor chip for conductivity measurement using Pt. Specifically, this sensor chip is configured to measure a change in conductivity on the basis of an ion concentration of a measuring object getting between two Pt wires that are formed parallel on a surface of a base material such as PET. Also, a sensor chip for ORP measurement in which only one Pt wire is formed on a surface may be used. Even in the case of using such a chip, the above-described embodiment can be configured. In short, as long as a sensor chip can be used as the measuring electrode, the effect of the present invention can be enjoyed. In addition, by appropriately selecting the sensor chip for electrochemical measurement as described above, the present invention can be configured as not only the pH sensor but various types of sensors for electrochemical measurement such as a conductivity sensor, an ORP sensor, and an ion concentration sensor.

In a lower part of the fore end surface in the above-described embodiment, a thermistor or the like may be arranged for temperature correction of a measured value. Also, the liquid junction part is not required to be exposed on the fore end surface, but may be exposed, for example, on a side surface in the fore end part of the body. Further, the fore end surface is not required to be wholly formed on the front surface of the substrate, but may be partially formed in the fore end part of the body. In short, it is only necessary to be at least the substrate in the periphery where the first through-hole for exposing the sensing part of the ISFET chip is formed, and thereby prevent the depth of the through-hole from being increased too much.

In addition, in the above-described embodiment, the pH sensor is cited as an example; however, the present invention may be adapted to, on the gate insulating film of the ISFET chip, form a film that selects ions other than protons, and thereby measure the other ion species.

In the above-described embodiment, the shape of the body is the substantially cylindrical shape, but may be another shape. The shape may be a prismatic shape, or the central axis may be bent. In short, the fore end surface is only required to be formed with being inclined with respect to the virtual surface that is vertical to the extending predetermined axis of the body in the fore end part of the body.

Besides, various modifications may be made or the embodiments may be combined without departing from the scope of the present invention.

INDUSTRIAL APPLICABILITY

According to the electrode assembly of the present invention, the fore end surface formed by the front surface of the substrate is formed with being inclined with respect to the axial direction of the body, and also without use of a lead, the output signal from the sensor chip is adapted to be taken out by the wiring formed on the back surface of the substrate to be thereby able to shallow, as much as possible, the depth of the through-hole for exposing the sensor chip on the fore end surface, so that even in the case of immersion in a liquid measuring object, a situation where the measurement cannot be made by accumulation of air bubbles in the exposed portion of the sensor chip can be prevented more surely than before.

The invention claimed is:

1. An electrode assembly comprising:
a rod-like body that extends along a predetermined axis;
a substrate that is formed with a first through-hole penetrating between a front surface and a back surface and attached to a fore end part of the body;
a sensor chip for electrochemical measurement, the sensor chip being provided between the body and the substrate and attached on the back surface of the substrate such that a sensing part is exposed outside from the first through-hole;
wiring printed on the back surface of the substrate; and
a filling material provided between the sensor chip and the back surface of the substrate, the filling material comprising an outer circumferential surface, and inner circumferential surface, and a filling material through-hole located radially inward from the inner circumferential surface;
wherein the sensor chip is flip-chip mounted on the back surface of the substrate such that the sensor chip is connected to the wiring printed on the back surface of the substrate so that the sensor chip outputs an output signal through the wiring printed on the back surface of the substrate;
the substrate is attached with being inclined with respect to the predetermined axis of the body, and thereby the front surface of the substrate forms at least a part of a fore end surface that is inclined with respect to the predetermined axis; and
wherein the inner circumferential surface of the filling material is sloped inward toward a center of filling material from a substrate side of the filling material to a sensor chip side of the filling material.

2. The electrode assembly according to claim 1, wherein:
the fore end part of the body has an outer circumferential portion that protrudes toward a fore end side of the body along the predetermined axis;
a back surface outer edge portion of the substrate is attached to the outer circumferential portion; and
relay wiring that is contained inside the body, extends from a base end side to the fore end side of the body, and is connected to the back surface of the substrate is further provided.

3. The electrode assembly according to claim 1, wherein an angle formed between a virtual plane that vertically intersects with the predetermined axis and the fore end surface is equal to 30 degrees or less.

4. The electrode assembly according to claim 1, wherein:
inside the body, a containing part that contains an internal electrode and internal liquid is formed; and
a liquid junction part that is formed with penetrating through the back surface and the front surface of the substrate from the containing part.

* * * * *